United States Patent [19]

Saksela et al.

[11] Patent Number: 5,674,680
[45] Date of Patent: Oct. 7, 1997

[54] METHODS FOR THE PROGNOSIS AND MONITORING OF AIDS

[75] Inventors: Kalle M. Saksela; David Baltimore, both of New York, N.Y.

[73] Assignee: The Rockefeller University, New York, N.Y.

[21] Appl. No.: 189,237

[22] Filed: Jan. 31, 1994

[51] Int. Cl.$^6$ .................. C12Q 1/70; C12Q 1/68; C12P 19/34; C07H 21/04

[52] U.S. Cl. .................. 435/5; 435/6; 435/912; 435/91.51; 536/23.72

[58] Field of Search .................. 435/5, 6, 91.2, 435/91.51; 536/23.72

[56] References Cited

PUBLICATIONS

Carruthers et al., 1993, Nucleic Acids Res. 21:2537–38.
Connor et al., 1993, J. Virol. 67: 1772–77.
Embertson et al., 1993, Nature 362:359–362.
Pantaleo et al., 1993, N. Engl. J. Med. 328:327–335.
Pantaleo et al., 1993, Nature 362:355–358.
Saksela et al., 1993, J. Virol 67:7423–27.
Bagnarelli et al., 1992, J. Virol. 66:7328–35.
CDC, 1992, MMWR 41 (RR–17):1–19.
Carruthers and Cross, 1992, Proc. Natl. Acad. Sci. USA 89:8818–21.
Ferre et al., 1992, AIDS Res. Hum. Retroviruses 8:269–275.
Seshamma et al., 1992, Proc. Natl. Acad. Sci. USA 89:10663–67.
Fox et al., 1991, J. Infect. Dis., 164:1051–57.
Klotman et al., 1991, Proc. Natl. Acad. Sci. USA 88:5011–15.
Pantaleo et al., 1991, Proc. Natl. Acad. Sci. USA 88:9838–42.
Schnittman et al., 1991, AIDS Res. Hum. Retroviruses 7:361–367.
Schnittman et al., 1990, Ann. Intern. Med. 113:438–443.
Mathez et al., 1990, Proc. Natl. Acad. Sci. USA 87:7438–42.
Ho et al., 1989, J. Engl. J. Med 321:1621–25.
Kim et al., 1989, J. Virol. 63:3708–13.
Schnittman et al., 1989, Science 245:305–308.
Allain et al., 1987, N. Eng. J. Med., 317:1114–1121.

Chomczynski and Sacchi, 1987, Anal. Biochem. 162:156–159.
Michael et al. J. Virol. 66 310–316 (1992) Viral DNA and mRNA expression correlate with the stage of Human . . . .
Hamilton et al. N. Engl. J. Med. 326 437–443 (1992) A controlled trial of early versus late treatment with zido vodine . . . .
Fahey et al. N. Engl. J. Med. 322 166–172 (1990) The prognostic value of cellular and serologic markers in infection . . . .

*Primary Examiner*—James Ketter
*Assistant Examiner*—John S. Brusca
*Attorney, Agent, or Firm*—Klauber & Jackson

[57] ABSTRACT

This invention relates to the prognosis of outcome of infection with the human immunodeficiency virus (HIV). In particular, the present invention concerns monitoring individuals who are at risk for developing acquired immunodeficiency syndrome (AIDS), and individuals who are undergoing therapy for AIDS. The method for estimating the risk of the onset of a clinical event associated with infection with HIV broadly comprises evaluating the rate of HIV replication in peripheral blood cells from an individual suspected of suffering from HIV infection. More particularly, the method comprises determining the level of expression of HIV messenger RNA (mRNA) in peripheral blood cells of an asymptomatic individual. High level expression of HIV mRNA indicates a high likelihood of onset of symptoms of AIDS, and low level expression or determination of no detectable expression indicates a low likelihood of onset of symptoms of AIDS. In a specific embodiment, the level of HIV-1 mRNA, specifically multiply spliced (MS) and unspliced (US) HIV mRNA, is detected in peripheral blood cells from HIV-infected individuals, and the detection of high levels of HIV mRNA is predictive of the onset of clinical symptoms associated with disease progression, including the diagnosis of AIDS, a decrease in the number of CD4+ cells to below 500 CD4+ cells per mm$^3$, and other clinical events. According to the invention, the onset of clinical AIDS generally occurs within about 2 years of the determination of high level expression of HIV mRNA, and the onset of clinical symptoms generally does not occur for at least about 5 years after the determination of no detectable expression of HIV mRNA.

37 Claims, 5 Drawing Sheets

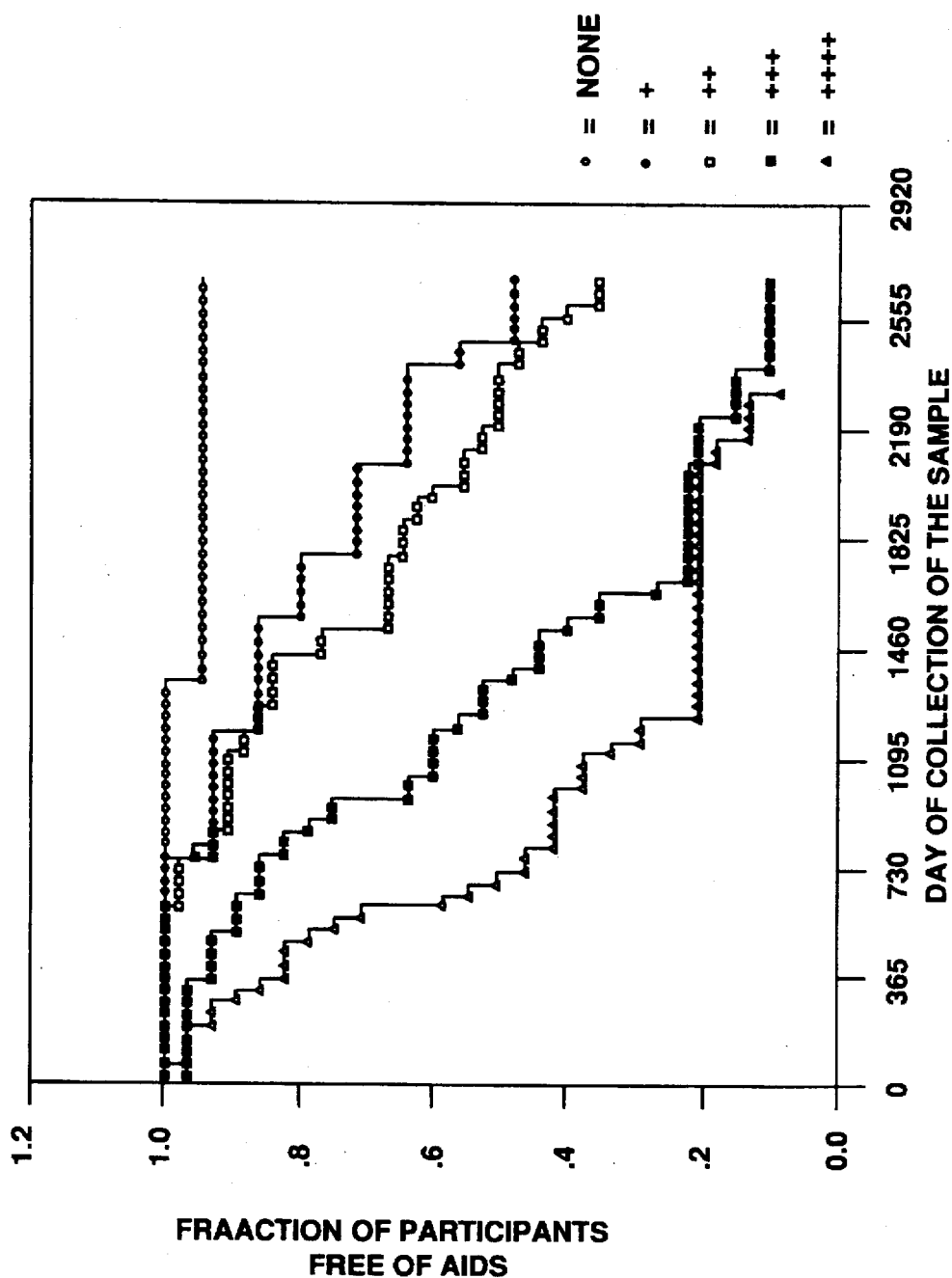

METHODS FOR THE PROGNOSIS AND MONITORING OF AIDS

The research leading to the present invention was funded in part by National Institutes of Health Grant AI2346, and the government may have certain rights in the invention.

FIELD OF THE INVENTION

This invention relates to the prognosis of outcome of infection with the human immunodeficiency virus. In particular, present invention concerns monitoring individuals who are at risk for developing acquired immunodeficiency syndrome (AIDS), and individuals who are undergoing therapy for AIDS.

BACKGROUND OF THE INVENTION

The pathogenesis of human immunodeficiency virus (HIV)-1 infection is characterized by a variable but often prolonged asymptomatic period following the acute viremic phase (Pantalco et at., 1993, N. Engl. J. Med. 328:327–335). Previous work has established a correlation between HIV disease progression and increasing amounts of infectious virus, vital antigens, and virus-specific nucleic acids (Allain et at., 1987, N. engl. J. Med. 317:1114–1121; Dagnarelli et at., 1992, J. Virol. 66:7328–35; Connor et at., 1993, J. Virol. 67:1772–77; Ferre et al., 1992, AIDS Res. Hum. Retroviruses 8:269–275; Ho et at., 1989, J. Engl. J. Med. 321:1621–25; Mathez et al., 1990, Proc. Natl. Acad. Sci. USA 87:7438–42; Michael et at., 1992, J. Virol. 66:310–316; Pantalco et al., 1993, Nature 362:355–358; Schnittman et at, 1989, Science 245:305–308; Schnittman et at., 1990, Ann. Intern. Med. 113:438–443; Schnittman et at., 1991, AIDS Res. Hum. Retroviruses 7:361–367). However, HIV mRNA, indicative of viral replication, has been demonstrated in cells at all stages of the disease, and it has been suggested that true microbiological latency at the cellular level may therefore not exist (Michael et at., supra; Schnittman et at., 1991, supra). In particular, active viral replication may occur in the lymphatic tissue throughout the clinically latent period (Pantalco et al., 1993, Nature supra, Fox et al., 1991, J. Infect. Dis. 164:1051–57; Pantalco et at., 1991, Proc. Natl. Acad. Sci. USA 88:9838–42; Embertson et al, 1993, Nature 362:359–362).

Therefore, the detection of viral replication has not to date provided an accurate prognostic indicator of the progress or severity of disease associated with HIV infection, i.e., acquired immunodeficiency syndrome (AIDS). More importantly, previous studies examining HIV replication in PBMC of infected individuals have not addressed the critical issue whether the differences in HIV mRNA levels correlate with the subsequent course of the disease.

The citation of references herein shall not be construed as an admission that such is prior art to the present invention.

SUMMARY OF THE INVENTION

The present invention is broadly directed to methods for estimating the risk of the on set of a clinical event associated with infection with human immunodeficiency virus (HIV) by evaluating the rate of HIV replication in peripheral blood cells from an individual suspected of suffering from HIV infection. These clinical events include (a) development of clinical signs of immunodeficiency; (b) a drop in the level of CD4-positive cells; and (c) death.

In particular aspects, the invention provides for prognosis of the severity of disease progression, and monitoring the course of AIDS. In one aspect of the invention, the rate of replication can be related to the level of expression of HIV mRNA in individuals who are infected or believed to be infected with HIV.

The invention differs from prior art methods in that the expression of HIV in peripheral blood cells is determined, rather than cell free HIV RNA, i.e., genomic RNA of infectious, defective, or degraded HIV particles.

In particular, the invention concerns a method for predicting the likelihood of onset of symptoms of acquired immunodeficiency syndrome (AIDS). The method broadly comprises determining the level of expression of human immunodeficiency virus (HIV) messenger RNA (mRNA) in peripheral blood cells of an asymptomatic individual. High level expression of HIV mRNA indicates a high likelihood of onset of symptoms of AIDS, and low level expression or determination of no detectable expression indicates a low likelihood of onset of symptoms of AIDS.

In particular aspects, the invention relates to the detection of the level of HIV-1 mRNA, specifically multiply spliced (MS), unspliced (US) or single-spliced (SS) HIV mRNA.

A particular advantage of the present invention is that the detection of high levels of HIV mRNA is predictive of the onset of clinical symptoms associated with disease progression, including the diagnosis of AIDS, a decrease in the number of CD4+ cells to below 500 CD4+ cells per $mm^3$, and other clinical events. According to the invention, the onset of clinical symptoms generally occurs within about 2 years of the determination of high level expression of HIV mRNA, and the onset of clinical symptoms generally does not occur for at least about 5 years after the determination of no detectable expression of HIV mRNA.

A particular advantage of the invention is that it is a highly accurate prognostic indicator of the progression of HIV-associated disease, e.g., the onset of symptoms of AIDS in HIV-positive individuals. The method requires only peripheral blood cells, in particular peripheral blood mononuclear cells (PBMC), in which the expression of HIV mRNA, which correlates to HIV replication, can be detected. The level of expression of HIV mRNA can be determined by quantitating the amount of HIV mRNA by polymerase chain reaction (PCR). In a specific embodiment, infra, reverse transcriptase-initiated PCR is used (see, e.g., Saksela et at., 1993, J. Virol. 67:7423–27). Previously, there has been no accurate prognostic indicator of the onset of AIDS symptoms in asymptomatic, HIV-positive, individual.

A corollary discovery of the inventors is that administration of a therapeutic treatment for AIDS can result in a detectable change in the level of HIV mRNA expression. In particular, it has been observed that 3'-azido-3'-deoxythymidine (AZT) therapy results in a transient decrease in the level of HIV mRNA expression.

Accordingly, the invention further relates to a method for monitoring a therapeutic treatment for AIDS comprising determining the level of expression of HIV mRNA in peripheral blood cells of an individual undergoing a therapeutic treatment for AIDS. A decrease in the level of expression of HIV mRNA compared to the individual at an earlier time is indicative of a regression of the AIDS, and an increase in the level of expression of HIV mRNA compared to the individual at an earlier time is indicative of progression of the AIDS.

The present invention further provides a method for monitoring the efficacy of a therapeutic treatment for HIV infection, by providing an accurate prognostic indicator of disease progression. This is very important for identifying possible therapeutic drugs and for monitoring patients undergoing therapies with these drugs.

In a specific aspect, the invention contemplates administration of an effective amount of an antiviral agent to the individual and monitoring the therapeutic outcome; in a more specific aspect, the antiviral agent is AZT.

The invention also provides an accurate method for detecting HIV replication for determining the optimal time for therapeutic intervention. For example, high level HIV replication detected in an individual indicates the need for fast, effective anti-viral therapy.

In yet a further embodiment, the invention relates to a method for monitoring the course of AIDS in an individual suffering from AIDS, comprising determining the level of expression of HIV mRNA in peripheral blood cells of an individual suffering from AIDS. A decrease in the level of expression of HIV mRNA compared to the individual at an earlier time is indicative of a regression of the AIDS, and an increase in the level of expression of HIV mRNA compared to the individual at an earlier time is indicative of progression of the AIDS.

The present invention addresses the need in the art for accurate prediction of disease course and severity in HIV-infected individuals. In specific examples, infra, HIV mRNA expression in serial cryopreserved PBMC samples from clinically well-characterized HIV-infected individuals collected over a 7-year period was examined. The examination showed that the rate of viral replication in PBMC correlates well with the subsequent clinical course of the infection.

In a further Example, infra, replication of HIV in PBMC during antiretroviral therapy was examined, and a significant but transient decrease in HIV-1 mRNA expression was observed when AZT therapy was initiated during the study.

Accordingly, it is an object of the present invention to permit accurate prognosis of the course of an HIV infection.

It is a further object of the invention to permit accurate prediction of the time of onset of the symptoms of AIDS.

Yet another object of the invention is to permit accurate monitoring of a therapy for AIDS.

It is yet another object of the invention to provide a method for monitoring the course of AIDS.

These and other objects of the present invention will be more completely understood by reference to the following detailed description and non-limiting Example, in conjunction with the accompanying drawings.

BRIEF DESCRIPTION OF THE DRAWINGS

FIG. 4. Fraction of Participants Free of AIDS (according to the CDCP classification) versus Day of Collection of the Sample. Participants were 150 individuals analyzed during a 7-year follow-up period after obtaining their initial blood samples. Day zero denotes the day that the initial sample was collected for each individual. "Day of Collection of the Sample" denotes the number of days after Day zero that subsequent samples were collected. The different groupings correspond to the relative amount of HIV-1 mRNA (MS and US mRNA) detected in PBMCs in the blood samples. The subgroupings relate to the number of plus signs (none to ++++) as shown in Table 1, with ○ corresponding to none; ● corresponding to +; □ corresponding to ++; ■ fraction of participants free of AIDS in each grouping, is depicted as a normalized value (with a value of 1.0 indicating that the participants in the group are 100% free of AIDS) and correlates strongly with the level of HIV-1 mRNA present in the PBMCs. The onset of AIDS in a small fraction of the samples that showed low or no expression of HIV-1 mRNA appears to be due to a sample mix-up.

DETAILED DESCRIPTION OF THE INVENTION

Figure 1A:
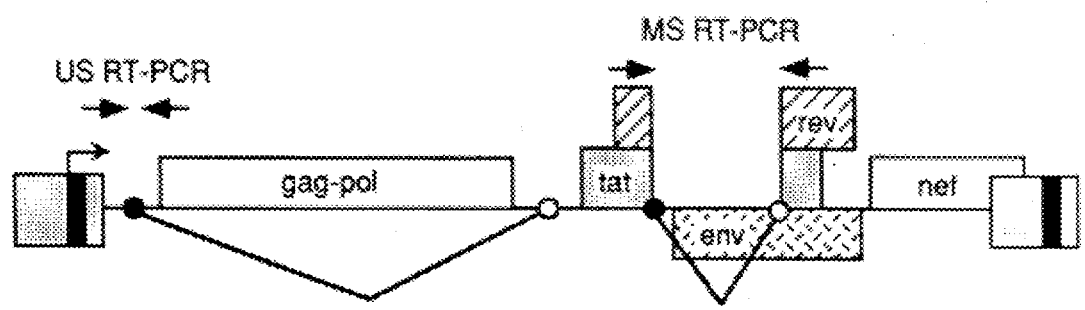
FIGS. 1A–1B. HIV-1 RT-PCR assay. (A) Schematic outline of HIV-1 structure illustrating the relevant viral genes and features of HIV-1 RNA mRNA splicing. The arrows indicate the location of the PCR primers chosen based on maximal HIV-1 sequence conservation and empirical evaluation for optimal performance in RT-PCR. (B) RT-PCR analysis of in vitro transcribed HIV-1 RNAs diluted in indicated amounts into a constant amount (1 µg) of total PBMC RNA from a HIV-negative donor. One femtogram (fg) of each control HIV RNA corresponds to approximately $4\times10^3$ copies of these molecules. A uniform efficiency of reverse transcription among the cDNA reactions is indicated by the comparable intensities of the PBMC-derived β-actin mRNA signals.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et at., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbat, *A Practical Guide To Molecular Cloning* (1984). Of particular relevance to the present invention are the recent descriptions of high-efficiency clonal growth of bloodstream- and insect-form *Trypanosoma brucei* on agarose plates (Carruthers and Cross, 1992, Proc. Natl. Acad. Sci. USA 89:8818–21) and DNA-mediated transformation of bloodstream-form *Trypanosoma brucei* (Carruthers et at., 1993, Nucleic Acids Res. 21:2537–38).

Therefore, if appearing herein, the following terms shall have the definitions set out below.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., 1989, supra). The conditions of temperature and ionic strength determine the "stringency" of the hybridization. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. Preferably a minimum length for a hybridizable nucleic acid is at least about 10 nucleotides; more preferably at least about 15 nucleotides.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences. Various splice acceptor sites are necessary for RNA splicing and are included herein within the definition of "control sequences." Some such sequences also play a role in the abundance and stage-specificity of gene expression.

Various abbreviations are used throughout this specification, and have the meanings defined as follows: HIV, human immunodeficiency virus; RT-PCR, reverse transcriptase-initiated polymerase chain reaction; PBMC, peripheral blood mononuclear cells; AZT, 3'-azido-3'-deoxythymidine (zivoduine); US, unspliced; MS, multiply spliced; SS, single-spliced; NYBC, New York Blood Center.

In its primary aspect, the present invention relates to a method for the prognosis of a risk of disease progression and prediction of its severity in HIV-infected individuals. The invention provides methods to predict the progress and severity of a future course of disease depending on the rate of replication of HIV in peripheral blood cells, in particular, in peripheral blood mononuclear cells (PBMCs).

Rate of replication of HIV in peripheral blood cells can be detected by any means known in the art for the detection of replication. For example, replication can be detected by measuring the level of expression of HIV mRNA. HIV mRNA expression can be detected by Northern hybridization analysis, using a labelled nucleic acid probe to hybridize to and thus detect the HIV mRNA. In another embodiment, HIV mRNA can be detected with a labelled nucleic acid probe in situ. In a further embodiment, dot blot analysis can be used to detect expression of HIV mRNA. The level of HIV mRNA expression can be measured by quantitating the label intensity, regardless of the technique use. For example, when the probe is labelled with a radioactive label, such as $^{32}$P, band density can be measured after autoradiography of a Northern analysis sample; the number of grains per cell can be measured after in situ hybridization; and the dot intensity can be measured by counting or by density analysis after dot blot hybridization.

In a preferred aspect of the invention, the level of HIV mRNA expression can be evaluated by PCR amplification. In a specific embodiment, reverse transcriptase-initiated PCR is used to detect the level of expression of HIV mRNA. However, any PCR technique can be used according to the present invention. Oligonucleotide primers corresponding to sequences of HIV mRNA can be prepared for use as primers in PCR. Preferably, such primers are prepared synthetically. Sequences for such oligonucleotide primers are readily available from the information known about HIV genomic sequences. Specific primers are provided in SEQ ID NOS: 1–4. The oligonucleotides may be utilized as primers to amplify by PCR mRNA obtained from peripheral blood cells. PCR can be carried out, e.g., by use of a Perkin-Elmer Cetus thermal cycler and Taq polymerase (Gene Amp™, Boehringer Mannheim). The amplified PCR products can be detected by incorporation of radionucleotides, e.g., $^{32}$P-labelled dCTP, or stained with ethidium bromide. However, according to the present invention, radionucleotide labels are preferred as these can yield more quantitative information, e.g., by analysis of band density after gel electrophoresis and autoradiography.

PCR amplification can overcome disadvantages of other methods that derive from the low frequency of cells that express HIV mRNA. For example, fewer than 1 in 1000 to 10,000 cells in a sample may be infected with HIV.

In a further preferred aspect of the invention, the amount of HIV mRNA present in a sample can be quantitated by comparing the total amount detected in the sample to the amount present in a control sample analyzed in parallel.

In a further embodiment, the level of expression of HIV mRNA can be compared to the level of expression of an endogenous cell mRNA, such as β-actin mRNA, as an internal control for each sample.

In yet a further embodiment, HIV replication can be detected by measuring the level of protein production, e.g., by detecting HIV protein expression using immunochemical or biochemical techniques.

Three types of HIV mRNA are found in peripheral blood cells: unspliced (US), multiply spliced (MS) and single-spliced (SS). According to the present invention, measurement of the level of expression of one or a combination of more than one of these types of HIV mRNA is indicative of the rate of HIV replication in the peripheral blood cells in the sample.

It has been found by the present inventors that the level of HIV replication provides an accurate indicator of disease progression and severity. Low or non-detectable HIV replication indicates continuation of an asymptomatic state for an indefinite period of approximately 5 years or longer. Moderate levels of HIV replication are incompatible with long term (greater than 5 years) maintenance of normal levels of CD4-positive lymphocytes. In a specific example, infra, the time between the last negative sample and the first measurement of less than 500 CD4-positive cells per $mm^3$ was never less than 2 years, and often much longer.

Increased severity of disease can correlate with a number of factors, including but not limited to development of clinical signs of immunodeficiency; a drop in the levels of CD4-positive cells, in particular a drop below 500 cells per $mm^3$; development of AIDS; and death.

Diagnosis of the development of AIDS can be made according to the criteria set forth by the Centers for Disease Control and Prevention (CDCP). As more becomes known about AIDS, the CDCP from time to time revises and publishes the criteria in Morbidity and Mortality Weekly, according to this knowledge. For example, the presence of an opportunistic infection was essential for making a diagnosis of AIDS. Recently, however, the criteria have expanded to include decrease in the level of CD4-positive lymphocytes to below 200 cells per $mm^3$. For example, see Centers for Disease Control and Prevention (1992, "1993 Revised classification system for HIV infection and expanded surveillance case definition for AIDS among adolescents and adults", MMWR 41(RR-17):1–19.

The present invention further provides for monitoring the course of an antiviral therapy for HIV. Various antiviral therapeutic agents for the treatment of HIV infection are known in the art, e.g., nucleotide analog-type inhibitors of the reverse transcriptase, such as but not limited to AZT (zidovudine, Retrovir), 2',3'-dideoxy-inosine (ddI, Videx), 2',3-dideoxycytidine (ddC, zalcitabine, HIVID). Many of these nucleotide analog inhibitors are in clinical trials; many more are being tested in laboratories for efficacy. Some nucleotide analogs in clinical trials include, but are not limited to, 3TC (Lamivadine), d4T (Stavudine), FLT, and PMEA. In a specific embodiment, the method of the invention was used to observe a transient decrease in the levels of HIV mRNA expression in individuals treated with AZT.

Other types of drugs and therapeutic strategies are also being tested for therapeutic effectiveness against HIV include but are not limited to the following: non-nucleotide analog inhibitors of reverse transcriptase, such as Nevirapine (BI-RG-587), TIBO (R82913), pyrinodes (such as R-697,661 and L-696,227), bis(heteroary)piperazines (BHAPs, such as U-87201E and U-90, 152), atevirdine mesylate (ATV) and R-89431; HIV protease inhibitors, include substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-IgG and CD4-PE40; blockers of HIV RNaseH activity, such as the AZT derivative azidothymidine monophosphate; drugs that alter the intracellular milieu to create conditions less favorable for viral replication, such as the free-radical scavengers and glutathione-level restoring drugs (N-acetylcysteine and similar drugs), and thalidomine (which seems to lower blood TNF-α levels; and manipulation of the immune system and viral replication with naturally occurring cytokines and lymphokines, or other agonists or antogonists of these systems. Accordingly, the present invention provides an accurate and effective prognostic assay for following the therapeutic effects of these drugs and therapeutic strategies for the treatment of HIV infection and AIDS.

The method of the present invention can be used for planning the optimal timing for administration of medications; choosing the most informative population for conducting drug trials for the treatment of HIV infection and AIDS; monitoring drug trials to evaluate the effectiveness of a particular therapeutic drug in the treatment of HIV infection or AIDS; and for providing a clinical prognostic evaluation for individuals who have or may have an HIV infection.

The invention will be further clarified by the following examples, which are intended to be purely exemplary of the invention.

EXAMPLE 1; HIV mRNA EXPRESSION PREDICTS DISEASE PROGRESSION

To address the significance of human immunodeficiency virus (HIV) replication in peripheral blood mononuclear cells (PBMC), reverse transcriptase-initiated polymerase chain reaction (RT-PCR) was used to measure HIV-1 mRNA expression in PBMC specimens collected from a cohort of HIV-infected individuals during a long-term prospective study. These measurements showed dramatic differences in HIV mRNA expression among individuals with very similar clinical and laboratory indices, and this variation strongly correlated with the future course of the disease. No evidence of viral replication was detected in PBMC from asymptomatic individuals who thereafter had normal levels of CD4+ cells for at least five years. Irrespective of whether the CD4+ cell numbers were normal at the time of sampling, abundant expression of HIV-1 mRNA in PBMC predicted accelerated disease progression within next two years. Thus, independently of what may be the rate of HIV replication in other viral reservoirs such as lymphatic tissue, the amount of HIV mRNA in PBMC appears to reflect the subsequent development of HIV disease. The results of the RT-PCR assay can also demonstrate a transient response to AZT treatment. Determination of HIV-1 mRNA expression in the PBMC of infected individuals, therefore, has significant clinical utility as a prognostic indicator and as a means to guiding and monitoring antiviral therapies.

Materials and Methods

Cryopreserved, Ficoll-Hypaque purified PBMC samples were thawed, washed with phosphate-buffered saline solution, and subjected to RNA extraction using the guanidium isothiocyanate/acid phenol method (Chomeczynski and Sacchi, 1987, Anal. Biochem. 162:156–159). The reverse transcriptase-initiated PCR (RT-PCR) procedures are summarized in FIG. 1A. A detailed description of these procedures and the primers used in found in Saksela et al. (1993, J. Virol. 67:7423–27). A brief summary of these procedures follows.

RNA preparations were treated for 1 hour with 100 U of RNase-free DNase (Boehringer Mannheim) in the presence of 50 U of placental RNase inhibitor (Boehringer Mannheim), extracted with phenol-chloroform, and precipitated with ethanol. High-molecular-weight DNA was extracted by standard methods and incubated for 1 hour with 100 U of boiled RNase A (Boehringer Mannheim) before addition of proteinase K to the lysates. Reverse RT-PCR analysis of the RNA samples was performed as follows. One microgram of DNase-treated RNA in 20 µl of water was heated for 5 min at 80° C., transferred onto ice, and combined with a mixture containing 6 µl of 5 X reaction buffer (250 mM Tris, pH 8.3, 375 mM KCl, 15 mM $MgCl_2$), 1.5 µl of deoxynucleoside triphosphates (dNTPs; 10 mM each), 0.6 µl of RNasin, 1 µl of random hexamers (1 mM, Pharmacia), and 2µ of Moloney murine leukemia virus reverse transcriptase (Gibco-BRL) or 2 µl of water in the control lacking enzyme. After 1 hour incubation at 42° C., 2 µl samples of the reverse transcription reactions were added to each 50-µl PCR mixture containing 10 mM Tris (pH 8.5), 50 mM KCl, 1.5 mM MgCl$_2$, 0.02% gelatin, 50 µM each unlabeled dNTP, 100 ng of each 23-mer oligonucleotide primer, 0.25 µl of [α-$^{32}$P]dCTP (3,000 Ci/mmol; NEN), and 0.25µ of Taq polymerase (5 U/ml; Boehringer). These reactions were cycled in tightly fitting tubes under mineral oil in a Perkin-Elmer Cetus DNA Thermal Cycler 480 as follows: one cycle of 94° C. for 40 s, 65° C. for 1 min, and 72° C. for 30 s; followed by 32 cycles of 94° C. for 20 s, 65° C. for 30 s, and 72° C. for 20 s. β-Actin PCRs were cycled only 22 times after the first cycle, using the conditions specified above, and 10% dimethyl sulfoxide was added to inhibit primer-dimer formation. The sequences (sense and antisense, respectively) of the oligonucleotides used were as follows:

unspliced (US) HIV-1:
5'-TCT CTA GCA GTG GCG CCC GAA CA-3' (SEQ ID NO:1)
5'-TCT CCT TCT AGC CTC CGC TAG TC-3' (SEQ ID NO:2)

multiply spliced (MS) HIV-1:
5'-CTT AGG CAT CTC CTA TGG CAG GAA-3' (SEQ ID NO:3)
5'-TTC CTF CGG GCC TGT CGG GTC CC-3' (SEQ ID NO:4)

β-actin
5'-CGA GCA GAG AGC CTC GCC TTT GC-3' (SEQ ID NO:5)
5'-CAT AGG AAT CCT TCT GAC CCA TG-3' (SEQ ID NO:6)

After gel electrophoresis and autoradiography, the intensities of the MS HIV and US HIV signals were compared with those of the control RNAs analyzed in parallel to estimate the approximate amounts of HIV-specific mRNAs present in the patient PBMC samples.

Results

To examine HIV replication in PBMC samples, RT-PCR assays specific for unspliced (US) and multiply-spliced (MS) HIV mRNA as well as cellular/β-actin mRNA were performed (FIG. 1A). US HIV RNA gives rise to Gag-Pol polyprotein, and is also packaged in virions as genomic HIV RNA. MS HIV mRNAs encode regulatory HIV proteins such as Tat and Rev, and are not present in virions in significant amounts, thus representing a good measure of ongoing vital replication in situ.

Figure 1B:
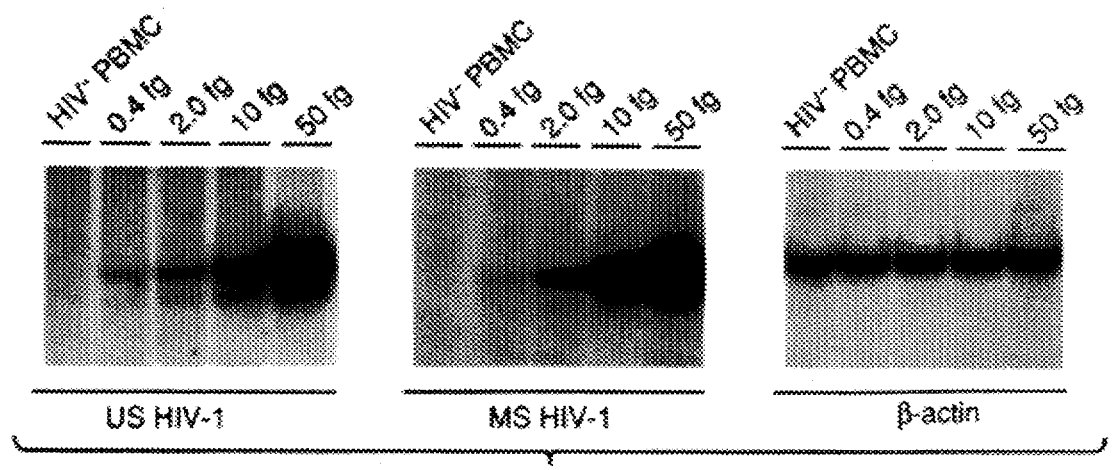

The RT-PCR of PBMC RNA samples was initiated by a step of random-primed cDNA synthesis followed by specific amplification of diagnostic DNA fragments in the presence of a radiolabeled nucleotide. The PCR products were then analyzed by gel electrophoresis and visualized by autoradiography. To estimate the number of HIV mRNA molecules in the patient samples and to confirm their quantitative amplification after reverse transcription, control samples were prepared by serially diluting known amounts of corresponding in vitro transcribed HIV RNAs into a constant amount of PBMC RNA prepared from an HIV-negative donor. FIG. 1B shows a typical result of an RT-PCR analysis of these control RNAs. To control for the amount and integrity of the RNAs prepared from different PBMC samples, as well as the uniform efficiency of their reverse transcription, a β-actin mRNA-specific fragment was also amplified from every cDNA preparation. Variation in the reverse transcription step between the different gene-specific PCR assays was minimized since this assay was based on random-primed reverse transcription, thus allowing the US HIV, MS HIV, and β-actin mRNAs all to be amplified from a single cDNA preparation.

This assay was used to quantitate US and MS HIV mRNA in serial cryopreserved PBMC samples collected from individuals involved in a long-term prospective study at the New York Blood Center (NYBC). The NYBC cohort includes 362 HIV-1 seropositive gay men who entered the study in 1984, 148 of whom had been followed since the late 1970's as a part of a hepatitis B study, allowing timing of seroconversion in 41 cases. Among these 362 men, 224 developed a disease meeting the CDC 1992 criteria for AIDS. Of the remaining, 79 men had evidence of immune deficiency (CD4+ cells<500 per mm$^3$) but did not develop AIDS, and 59 retained normal CD4+ cell numbers throughout the study.

Figure 2A:
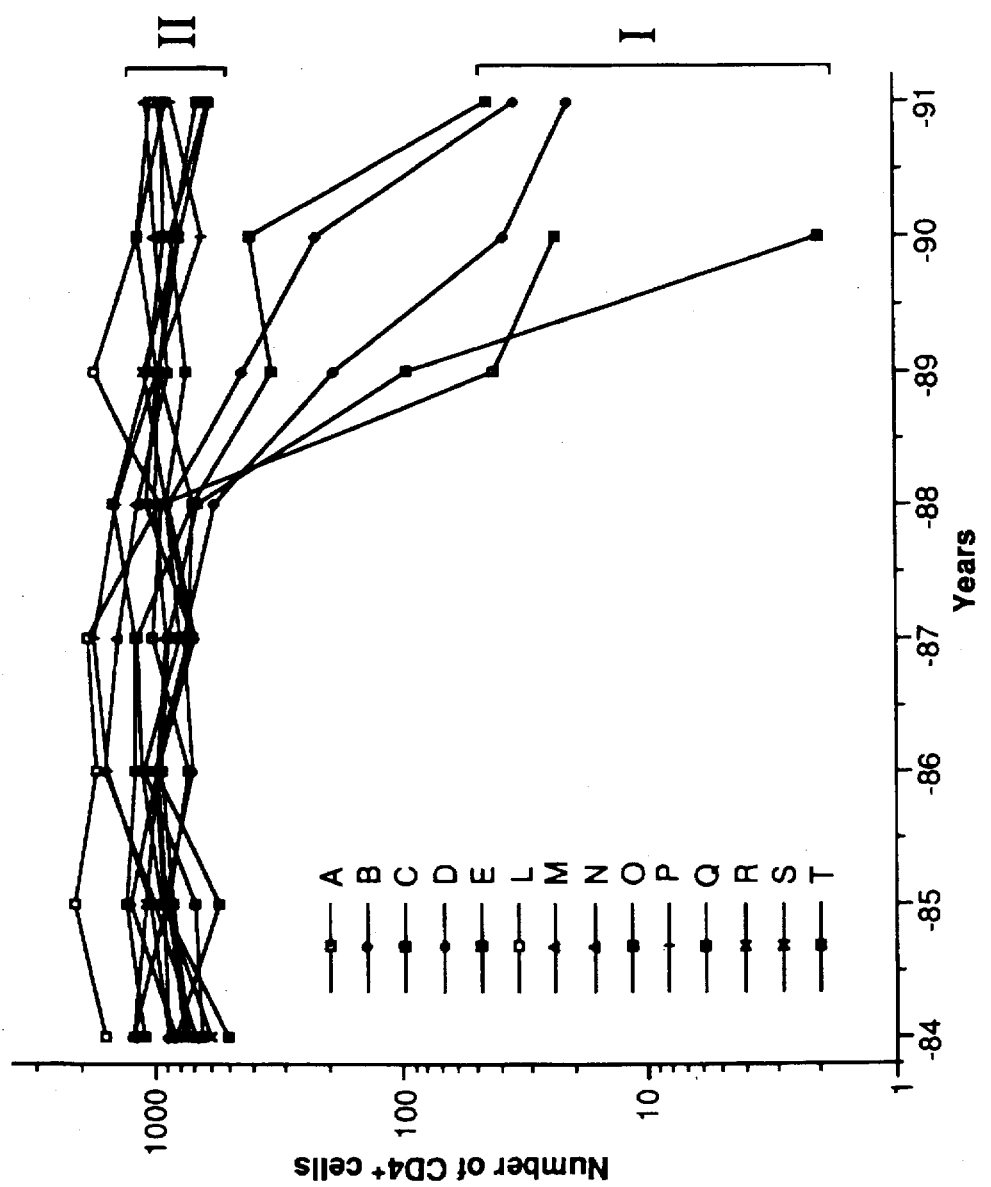
FIGS. 2A–2B. (A) CD4+ cell measurements of 14 individuals during a 7-year follow-up shown on a semilogarithmic scale. The alphabetical codes correspond to those in Table 1, infra. (B) RT-PCR analysis of US HIV-1, MS HIV-1 mRNA, and cellular β-actin mRNA in PBMC samples from the 14 individuals included in FIG. 2A. Each sample was collected at a time when CD4+ cell numbers were normal, as indicated in the parentheses above the corresponding lanes of the gel.

The present study was prompted by an initial examination of a small number of PBMC samples from individuals who experienced different clinical courses of HIV infection. It revealed abundant HIV mRNA expression in samples from patients with an advanced disease, whereas a large variation was observed in samples from asymptomatic individuals. To address the significance of this variation, 18 individuals were selected from the NYBC cohort, all of whom were initially asymptomatic and had very similar clinical and laboratory indices, but whose future course of disease during the subsequent years of follow-up fell into two contrasting patterns (Table 1 and FIG. 2A).

TABLE 1

Summary of the RT-PCR analyses of HIV-1 mRNA expression in sequential PBMC samples from 18 HIV-infected individuals during a 7-year follow-up period.

| ID | Date | CD4+ cells, no. | HIV mRNA US | HIV mRNA MS | ID | Date | CD4+ cells, no. | HIV mRNA US | HIV mRNA MS | ID | Date | CD4+ cells, no. | HIV mRNA US | HIV mRNA MS |
|---|---|---|---|---|---|---|---|---|---|---|---|---|---|---|
| Disease progression after a period with normal numbers of CD4+ cells | | | | | | | | | | | | | | |
| A | 01/30/85 | 914 | ++ | + | C | 02/27/85 | 881 | + | − | E | 08/12/84 | 998 | + | − |
|  | 01/19/87 | 1050 | +++ | ++ |  | 06/10/86 | 713 | + | + |  | 03/23/86 | 678 | + | − |
|  | 09/20/87 | 645 | ++ | + |  | 03/11/87 | 909 | + | + |  | 04/26/87 | 1039 | + | ++ |
|  | 01/24/88 | 972 | ++ | ++ |  | 07/21/87 | 755 | + | ++ |  | 01/24/88 | 725 | ++ | + |
|  | 06/15/88 | 72 | +++ | ++ |  | 07/24/88 | 572 | + | + |  | 06/12 88 | 441 | + | + |
|  | 10/16/88* | 99 | ++ | + |  | 09/25/88 | 703 | +++ | ++ |  | 11/13/88 | 461 | +++ | +++ |

TABLE 1-continued

Summary of the RT-PCR analyses of HIV-1 mRNA expression in sequential PBMC samples from 18 HIV-infected individuals during a 7-year follow-up period.

| ID | Date | CD4+ cells, no. | HIV mRNA US | MS | ID | Date | CD4+ cells, no. | HIV mRNA US | MS | ID | Date | CD4+ cells, no. | HIV mRNA US | MS |
|---|---|---|---|---|---|---|---|---|---|---|---|---|---|---|
|  | 02/26/89 | 43 | +++ | + |  | 11/29/88 | 152 | ++ | ++ |  | 06/18/89 | 345 | ++++ | +++ |
|  | 11/19/89 | 24 | +++ | + |  | 04/09/89* | 98 | + | + |  | SC < 3/83 |  |  |  |
|  | SC ≦ 10/84 | AZT 10/84 |  |  |  | 10/01/89 | 29 | ++ | + | F | 09/04/84 | 728 | + | − |
| B | 09/10/84 | 1691 | + | + |  | 05/22/90 | 2 | +++ | − |  | 07/27/86 | 660 | + | + |
|  | 01/28/85 | 950 | + | ++ |  | SC 8–10/84 | AZT 01/28/89 |  |  |  | 11/02/88 | 598 | ++ | + |
|  | 02/18/86 | 732 | + | ++ | D | 08/07/84 | 1076 | + | + |  | 04/16/91 | 188 | +++ | + |
|  | 01/07/87 | 793 | ++ | + |  | 04/30/85 | 1480 | + | + |  | SC ≦ 1979 |  |  |  |
|  | 10/26/87 | 798 | ++ | + |  | 09/01/87 | 986 | + | + | G | 12/17/84 | 1122 | + | + |
|  | 04/19/88 | 598 | ++ | +++ |  | 05/31/88 | 920 | +++ | +++ |  | 03/11/86 | 969 | + | + |
|  | 07/25/88 | 263 | +++ | +++ |  | 02/14/89 | 457 | +++ | ++ |  | 07/06/86 | 665 | + | + |
|  | 09/06/88 | 258 | +++ | +++ |  | 07/31/90* | 385 | +++ | ++ |  | 04/27/87 | 1199 | + | + |
|  | 03/13/89* | 194 | + | + |  | 04/23/91 | 35 | +++ | + |  | 10/09/88 | 610 | + | ++ |
|  | 07/24/89 | 136 | ++ | + |  | SC ≦ 06/80 | AZT 04/01/89 |  |  |  | 02/19/89 | 252 | +++ | +++ |
|  | 04/16/90 | 39 | ++ | + |  |  |  |  |  |  | 04/09/89 | 117 | ++ | ++ |
|  | 03/12/91 | 21 | +++ | + |  |  |  |  |  |  | *11/12/89* | 92 | ++ | + |
|  | SC < 4/84 | AZT 01/13/89 |  |  |  |  |  |  |  |  | 08/05/90 | 54 | ++ | + |

No apparent disease progression during the study

| ID | Date | CD4+ cells, no. | HIV mRNA US | MS | ID | Date | CD4+ cells, no. | HIV mRNA US | MS | ID | Date | CD4+ cells, no. | HIV mRNA US | MS |
|---|---|---|---|---|---|---|---|---|---|---|---|---|---|---|
| H | 12/17/84 | 1335 | − | − | L | 09/11/84 | 1034 | − | − | P | 11/05/84 | 1293 | − | − |
|  | 02/03/88 | 997 | − | − |  | 06/04/85 | 1493 | − | − |  | 07/31/85 | 1320 | − | − |
|  | 02/06/91 | 1080 | − | − |  | 01/29/91 | 894 | + | + |  | 08/06/91 | 1016 | − | − |
|  | SC ≦ 3/84 |  |  |  |  | SC ≦ 3/79 |  |  |  |  | SC 2–5/80 |  |  |  |
| I | 08/06/84 | 1089 | − | − | M | 08/12/84 | 1266 | − | − | Q | 01/29/85 | 1458 | − | − |
|  | 09/09/85 | 1573 | − | − |  | 04/21/85 | 1287 | − | − |  | 03/06/88 | 1955 | − | − |
|  | 02/04/91 | 623 | − | − |  | 04/17/91 | 975 | − | − |  | 10/08/91 | 1418 | + | + |
|  | SC ≦ 3/84 |  |  |  |  | SC ≦ 3/79 |  |  |  |  | SC ≦ 5/84 |  |  |  |
| J | 01/29/85 | 1042 | − | − | N | 07/31/84 | 817 | + | − | R | 06/17/85 | 759 | − | − |
|  | 09/23/85 | 783 | − | − |  | 08/27/85 | 952 | + | − |  | 05/07/90 | 468 | − | − |
|  | 09/09/91 | 1137 | − | − |  | 08/06/91 | 1159 | ND | ND |  | 04/06/91 | 607 | ND | ND |
|  | SC ≦ 4/84 |  |  |  |  | SC ≦ 4/79 |  |  |  |  | SC 8/84–1/85 |  |  |  |
| K | 10/15/84 | 830 | + | − | O | 02/04/85 | 733 | − | − |  |  |  |  |  |
|  | 08/07/85 | 1378 | − | − |  | 04/01/86 | 1173 | − | − |  |  |  |  |  |
|  | 02/06/91 | 544 | ++ | + |  | 01/27/91 | 548 | − | − |  |  |  |  |  |
|  | SC ≦ 1979 |  |  |  |  | 04/08/92 | 694 | ND | ND |  |  |  |  |  |
|  |  |  |  |  |  | SC ≦ 5/89 |  |  |  |  |  |  |  |  |

US and MS HIV-1 mRNA as well as cellular b-actin mRNAs were measured from each sample as described in FIG. 1. ++++ indicates an amount of HIV mRNA corresponding to more than $1\times10^5$ copies of in vitro transcribed control RNA molecules per microgram of PBMC RNA. Similarly, +++ corresponds to $0.2-1\times10^5$; ++ to $0.5-2\times10^4$; + to $1-5\times10^3$; and − to less than $1\times10^3$ copies respectively. The date and the CD4+ cell number at the time of sampling are shown. In three cases (N, O, R) an additional CD4+ measurement is shown to illustrate the subsequent course of the disease even if HIV mRNA expression was not determined (n.d.). SC denotes the approximate time when, or before which (≦), seroconversion occurred. When applicable, the date when AZT treatment was initiated is shown, and the first post-AZT specimen is marked with an asterisk (*).

All 18 individuals included in the study continued to have normal numbers of CD4+ cells during the first three years of the follow-up at NYBC. Thereafter 7 of them (A-G, group I) developed CD4+ lymphocytopenia and AIDS, whereas the other 11 (H-R, group II) continued to have normal CD4+ cell levels and were still asymptomatic when the study was discontinued in 1991.

Figure 2B:
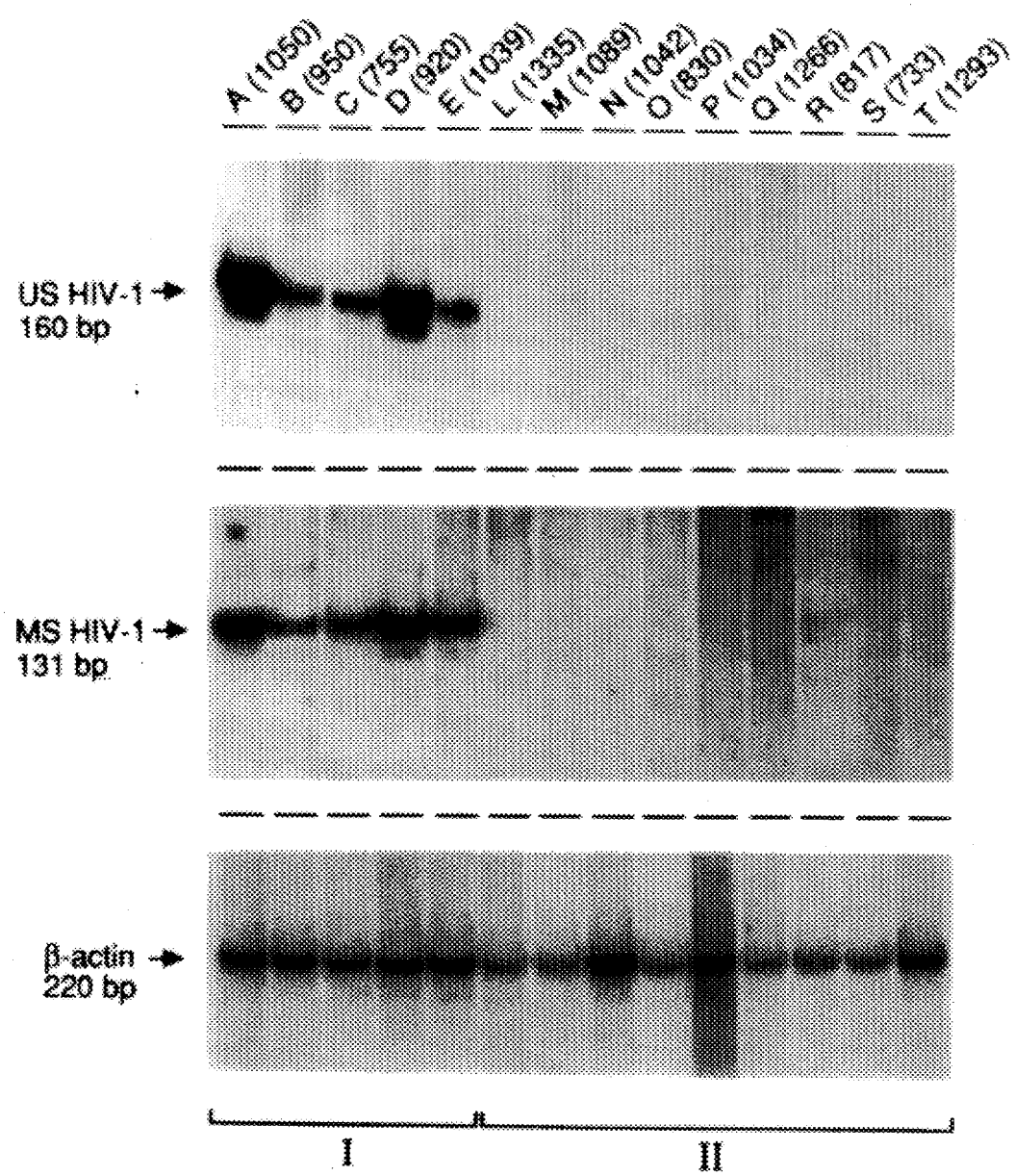

The first samples from each individual, from which their HIV gene expression pattern was established, were always analyzed in a blinded manner, such that the clinical data were disclosed only after the RT-PCR results were documented. Additional samples from each individual were then examined to define in more detail the temporal aspects of HIV mRNA expression over years. FIG. 2B shows the results from RT-PCR assays of representative PBMC specimens from the 14 individuals included in FIG. 2A, while the entire data base of RT-PCR results is summarized in Table 1. These data reveal a strong correlation between HIV replication in PBMC and the future clinical course of HIV infection. None of the samples from individuals who continued to have normal numbers of CD4+ cells during the subsequent 5 years (H-R) expressed a detectable amount of MS HIV-1 mRNA, which would indicate vital replication in these cells (Table 1 and FIG. 2B). In two cases (K, N) a faint US mRNA, but no MS HIV, signal, was detectable after long autoradiographic exposures (not shown). Expression of both US and MS HIV-1 RNA was readily detected in all PBMC specimens collected from individuals whose number of CD4+ cells thereafter declined below 500 per $mm^3$ within two years of sampling. Abundant expression of either HIV mRNA species (+++ or more in Table 1) appeared predictive of active disease progression, and was in every case followed by a significant drop in the number of CD4+ cells during the next 1–2 years. Thus, as illustrated by the data in FIG. 2, HIV replication in blood cells does not strictly correlate with the clinical stage of HIV infection. Rather, dramatic differences in HIV mRNA expression levels between individuals in the asymptomatic phase of the infection were observed, and this variation strongly correlated with the clinical course of their disease over the subsequent 1–3 years.

As expected, abundant expression of both US and MS HIV-1 mRNA was observed in most samples from individuals with decreased CD4+ cells or AIDS (Table 1). When patients became extensively CD4+ lymphocytopenic, a relative loss of MS HIV-1 mRNA expression was observed, while expression of US mRNA still remained high (e.g., individual C). Cell culture studies have indicated that MS HIV-1 mRNA is expressed predominantly early after HIV infection (Kim et at., 1989, J. Virol. 63:3708-13; Klotman et at., 1991, Proc. Nat. acad. Sci. USA 88:5011-15). Thus, the low levels of MS HIV mRNA in some PBMC samples probably reflects inefficient vital spread due to few remaining susceptible uninfected target cells. Also, some of the intense US HIV RT-PCR signals in such samples may be derived from genomic RNA of virions associated with the PBMCs rather than from US HIV mRNA produced in these cells.

Figure 3:
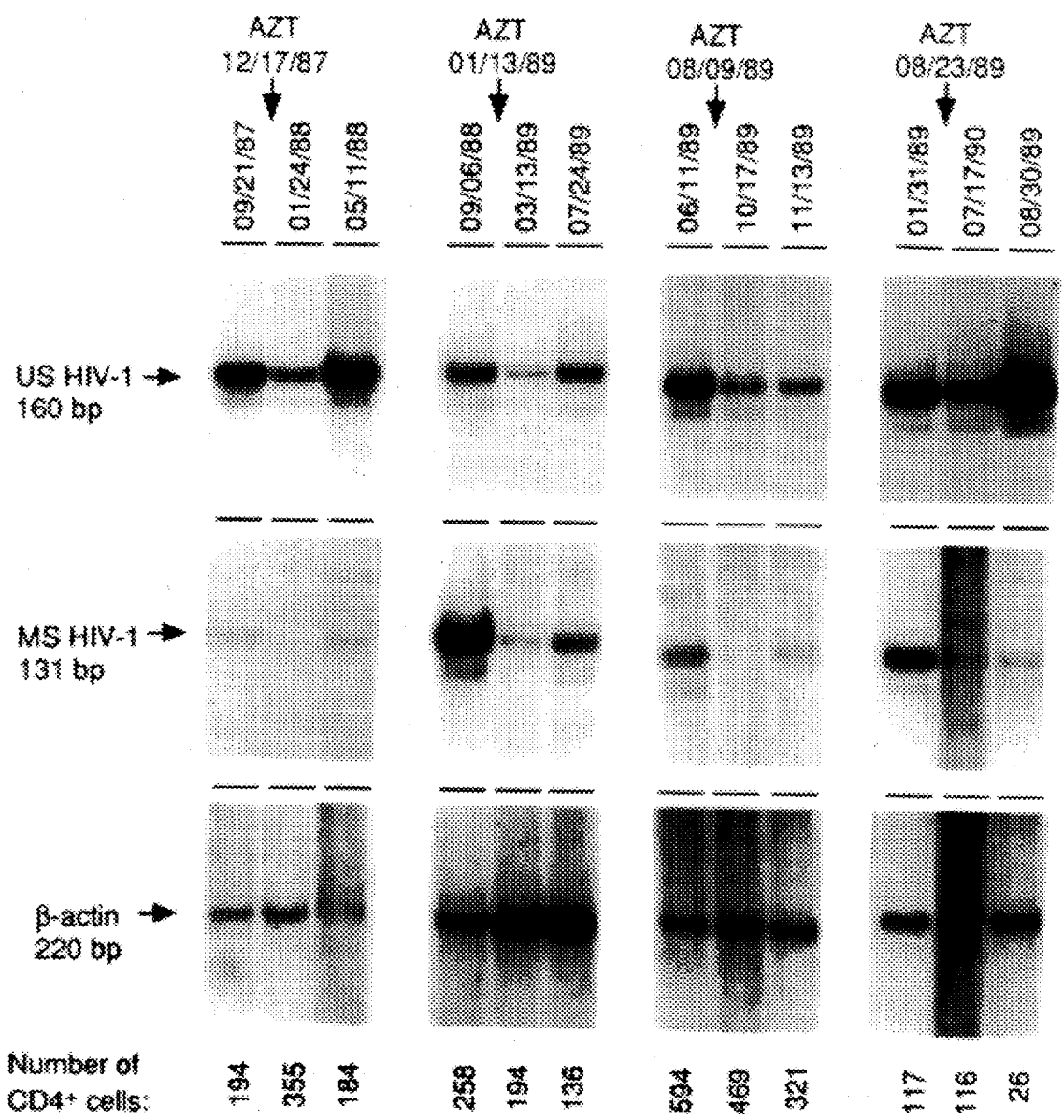
FIG. 3. HIV-1 mRNA expression in sequential PBMC samples from four patients obtained before and after initiation of AZT therapy. As indicated, AZT treatment was started between the collection of the first and the second sample. The dates of sampling and the corresponding measurements of CD4+ cells are also shown. The second panel from the left corresponds to patient B in Table 1, infra.

To study the effects of antiretroviral therapy on vital replication in PBMC and to test the possibility that the US and MS HIV mRNA species would be derived from cells with substantially different turnover rates, we also focused on samples collected shortly before and after the initiation of AZT therapy. For this purpose, in addition to the 18 originally selected individuals included in Table 1, serial samples from three other AZT-treated individuals were also analyzed (FIG. 3). When AZT treatment was initiated in the interval between the collection of two PBMC samples, a significant decrease in HIV expression was usually observed (Table 1 and FIG. 3). Little or no effect on HIV mRNA expression was seen in one ease, probably because AZT was initiated 4 months before the first post-AZT sample was obtained (Table 1, patient D). Despite continuous antiviral therapy, the favorable effect of AZT was typically lost within 4–6 months after treatment initiation. These results correlate with the limited benefit of AZT in the treatment of HIV infection (Johnston and Hoth, 1993, Science 260:1286–93), and indicate that determination of HIV-1 mRNA expression in PBMC could be useful in directly evaluating the effects of antiretroviral therapies and in monitoring the subsequent emergence of drug-resistant virus replication.

The decreased HIV-1 expression after the initiation of AZT therapy also suggests that both US and MS HIV mRNA species are derived from cells with a relatively rapid turnover rate. In contrast to a previous report (Seshamma et at., 1992, Proc. Natl. Acad. Sci. USA 89:10663–67), the present results showed no evidence of latently-infected cells expressing abundant MS HIV-1 mRNA but no US HIV-1 mRNA. Rather, any detectable MS HIV mRNA in PBMC appeared to be incompatible with a long-term (5 years) maintenance of normal levels of CD4+ cells. The absence of MS HIV mRNA, however, did not always indicate that an individual would remain progression-free, because early samples from certain individuals who later experienced disease progression were also found to be negative (C, E, F). Also, readily detectable expression of both US and MS HIV mRNA was observed in recent samples from three of the 11 long-term asymptomatic individuals (K, L, Q), suggesting eventual activation of their disease. Nevertheless, lack of MS HIV mRNA correlated in all cases with a benign proximal course of the disease: the time between the last sample negative for MS HIV-1 mRNA and the first CD4+ measurement lower than 500 per mm3 was never shorter than 2 years and often much longer.

Discussion

The present data show that increased expression of HIV mRNA in PBMC substantially precedes clinically defined progression of the disease. A longitudinal study addressing the rate of HIV replication in PBMC has not been previously reported, but results from two studies quantitating vital load during HIV infection are available (Connor et at, 1993, J. Virol. 67:1772–77; Schnittman et al., 1990, Ann. Intern. Med. 113:438–443). Both of these studies reported a correlation between viral load and the current disease status but suggested that an increase in viral load could also precede clinical progression of the disease. Vital load in an infected individual is determined by the opposing effects of viral replication and removal of productively infected cells and cell-free HIV. Thus, active HIV replication could occur for long times without an accompanying increase in the overall viral load.

The present results define a distinct period late during the asymptomatic phase of HIV infection which is characterized by active viral replication in the blood cells in the absence of apparent signs of the immune system destruction. Identification of such a phase of subclinical disease progression may help to characterize the pathogenic process by which HIV infection leads to immunodeficiency, and also could have important therapeutic implications.

The underlying causes that activate HIV replication in PBMC remain unclear. Also, whether the low (undetectable) level of viral mRNA expression observed in the blood cells of some long-term asymptomatic individuals is more due to a particularly effective anti-HIV immune response or a lesser replicative potential of the virus in these individuals remains an important question. The relation of the present findings to the recently-recognized active infection in the lymphatic tissues of asymptomatic individuals with little vital replication in their PBMC (Pantalco et at., 1993, Nature 362:355–358)) is yet another issue which needs to be addressed. It has been suggested that active viral replication in PBMC would indicate that significant damage in the lymphatic tissues has already occurred (Pantaim et al., 1993, N. Engl. J. Med. 328:327–335).

In contrast to the conclusions of an earlier study (Seshamma et al. 1992, Proc. Natl. Acad. Sci. USA 89:10663–67), we found no correlation between a specific HIV mRNA splicing pattern and clinical latency of HIV infection. Our results preclude the conclusion that long-lived, latently-infected cells expressing some (MS) but not all (US) HIV mRNA species represent a significant vital reservoir in asymptomatic HIV-infected individuals. Previous studies (Bagnarelli et at, 1992, J. Virol. 66:7328–35; Michael et at., 1992, J. Virol. 66:310–316; Pantalco et at., 1993, Nature 362:355-358) suggested that viral mRNA can be readily detected in the PBMC of most, if not all, infected individuals. However, by selecting a population including many individuals who remained progression-free for several years, we found that many PBMC specimens from HIV-infected individuals have no apparent expression of HIV mRNA. Unlike the material examined by us, a panel of PBMC samples from a randomly selected group of HIV-infected individuals would be expected to include few relatively early samples from such long-term asymptomatic individuals. However, it can not be ruled out that the sensitivity of an RT-PCR assay used in other studies could be greater. Therefore, it is important to point out that the threshold of detection of HIV mRNAs is not crucial to the present conclusions, as they are derived from ratios of signals at various times of sampling.

Besides their implications for the pathogenic process of HIV infection, our data also suggest that quantitation of HIV mRNA in PBMC has significant clinical utility as a prognostic indicator. The HIV RT-PCR assay was found to reliably distinguish individuals who have otherwise identical laboratory and clinical indices but who will subsequently experience contrasting clinical courses of infection. Based on our data it is safe to conclude that, independently of the current CD4+ cell numbers, the prognosis for the next three years of an individual with undetectable levels of PBMC HIV mRNA differs dramatically from that of an individual showing abundant HIV mRNA expression. Such prognostic information is clinically valuable, for example in examining individuals involved in trials testing antiretroviral therapies, and perhaps in the future, in optimal targeting of such therapies.

EXAMPLE 2; PREDICTION OF DISEASE SEVERITY IN A LARGE COHORT

Using the RT-PCR technique described above, a larger study of the level of HIV-1 expression in PBMCs from 150 HIV-infected individuals who had not yet developed AIDS at the time of sample collection was undertaken. The blood samples were randomly selected from the samples obtained in connection with the NYBC study from which the 18 samples described in Example 1 were obtained.

In this Example, a 150 single 1984 or 1985 samples from the cohort were randomly selected. This larger study was also blinded, as samples were analyzed without knowledge of the subsequent clinical information about each of the individuals. The subsequent clinical information was only revealed after all of the RT-PCR data were obtained and documented.

The results of this larger study are summarized in FIG. 4. Samples were divided in subgroups, each including samples from approximately 30 individuals. The subgroupings were made based on the HIV-1 mRNA expression in peripheral blood cells at the time of sample collection, i.e., 1984/1985. The subgroupings relate to the number of plus signs (none to ++++) as shown in Table 1.

Although not reported evident from the graph, the results shown in FIG. 4 were independent of other markers of HIV infection and AIDS, particularly the number of circulating CD4-positive lymphocytes. Thus, detection of HIV replication provides a much more informative prognostic indicator of disease course and severity than other possible measures, such as CD4-positive cell number.

The present invention is not to be limited in scope by the specific embodiments described herein since such embodiments are intended as but single illustrations of one aspect of the invention. Indeed, various modifications of the invention in addition to those shown and described herein will become apparent to those skilled in the art from the foregoing description and accompanying drawings. Such modifications are intended to fall within the scope of the appended claims.

Various references are cited herein, the disclosures of which are incorporated by reference herein in their entirety.

---

What is claimed is:

1. A method for predicting the time of onset of the development of clinical signs of immunodeficiency associated with disease progression in an individual infected with human immunodeficiency virus (HIV) comprising:
   (a) determining a level of expression of HIV messenger RNA (mRNA) in peripheral blood cells obtained from the individual; and
   (b) correlating the level of expression of HIV messenger RNA with the time of onset of the development of clinical signs of immunodeficiency; wherein
      (i) a high level of HIV mRNA correlates with a high likelihood for the development of clinical signs of immunodeficiency within about two years; and
      (ii) a low level of HIV mRNA or no detectable HIV mRNA correlates with a low likelihood of the development of clinical signs of immunodeficiency for at least five years.

2. The method according to claim 1, wherein the clinical signs of immunodeficiency are the current Centers for Disease Control and Prevention (CDCP) criteria for a diagnosis of acquired immunodeficiency syndrome (AIDS).

3. The method according to claim 1 wherein the HIV is HIV-1.

4. The method according to claim 1 wherein the HIV mRNA is selected from the group consisting of multiply spliced (MS), unspliced (US), and single-spliced (SS) HIV mRNA.

5. The method according to claim 1 wherein the level of expression of HIV mRNA is determined by quantitating the amount of HIV mRNA by polymerase chain reaction (PCR).

6. The method according to claim 5, further comprising comparing the amount of HIV mRNA determined by polymerase chain reaction with an mount of a control RNA in parallel.

7. A method for predicting the time of occurrence of a drop in the level of CD4-positive T-cells associated with disease progression in an individual infected with human immunodeficiency virus (HIV) comprising:
   (a) determining a level or expression of HIV messenger RNA (mRNA) in peripheral blood cells obtained from the individual; and
   (b) correlating the level of expression of HIV messenger RNA with the time of a drop in the level of CD4-positive T-cells; wherein
      (i) a high level of HIV mRNA correlates with a high likelihood for a drop in the level of CD4-positive T-cells within about two years; and
      (ii) a low level of mRNA or no detectable mRNA correlates with a low likelihood for a drop in the level of CD4-positive T-cells for at least five years.

8. The method according to claim 7 wherein the HIV is HIV-1.

9. The method according to claim 7 wherein the HIV mRNA is selected from the group consisting of multiply spliced (MS), unspliced (US), and single-spliced (SS) HIV mRNA.

10. The method according to claim 7 wherein the level of expression of HIV mRNA is determined by quantitating the amount of HIV mRNA by polymerase chain reaction.

11. The method according to claim 10 further comprising comparing the amount of HIV mRNA determined by polymerase chain reaction with an amount of a control RNA in parallel.

12. A method for predicting the time of the onset of death associated with disease progression in an individual infected with human immunodeficiency virus (HIV), comprising:
   (a) determining a level of expression of HIV messenger RNA (mRNA) in peripheral blood cells obtained from the individual; and
   (b) correlating the level of expression of HIV messenger RNA with a prognosis for the time of onset of death; wherein a low level of HIV mRNA or no detectable HIV mRNA correlates with a low likelihood of the onset of death for at least five years.

13. The method according to claim 12 wherein the HIV is HIV-1.

14. The method according to claim 12 wherein the HIV mRNA is selected from the group consisting of multiply spliced (MS), unspliced (US), and single-spliced (SS) HIV mRNA.

15. The method according to claim 12 wherein the level of expression of HIV mRNA is determined by quantitating the amount of HIV mRNA by polymerase chain reaction.

16. The method according to claim 15 further comprising comparing the amount of HIV mRNA determined by polymerase chain reaction with an amount of a control RNA in parallel.

17. A method for monitoring a therapeutic treatment for AIDS comprising determining a level of expression of HIV messenger RNA (mRNA) in peripheral blood cells of an individual undergoing a therapeutic treatment for AIDS, comprising:
   (a) determining a level of expression of HIV messenger RNA in peripheral blood cells obtained from the individual; and
   (b) correlating the level of expression of HIV messenger RNA with the time of a drop in the level of CD4-positive T-cells; wherein
      (i) detectable HIV mRNA correlates with a high likelihood for a drop in the level of CD4-positive T-cells below normal levels within about five years; and
      (ii) no detectable HIV mRNA correlates with a low likelihood for it drop in the level of CD4-positive T-cells below 500 per $mm^3$ for at least two years.

18. The method according to claim 17, wherein the therapeutic treatment comprises administration of an effective amount of an antiviral agent to the individual.

19. The method according to claim 18, wherein the antiviral agent is 3'-azido-3'-deoxythymidine (AZT).

20. The method according to claim 17, wherein the HIV is HIV-1.

21. The method according to claim 17, wherein the HIV mRNA is selected from the group consisting of multiply spliced (MS), unspliced (US), or single-spliced (SS) HIV mRNA.

22. The method according to claim 21, wherein the level of expression of HIV mRNA is determined by quantitating the amount of HIV mRNA by polymerase chain reaction.

23. The method according to claim 23, further comprising comparing the mount of HIV mRNA determined by polymerase chain reaction with an amount of a control RNA in parallel.

24. A method for monitoring a therapeutic treatment for AIDS comprising determining a level of expression of HIV messenger RNA (mRNA) in peripheral blood cells of an individual undergoing a therapeutic treatment for AIDS, comprising:
   (a) determining a level of expression of HIV messenger RNA in peripheral blood cells obtained from the individual; and
   (b) correlating the level of expression of HIV messenger RNA with the time of onset of the development of clinical signs of immunodeficiency; wherein (i) detectable HIV mRNA correlates with a high likelihood for the development of clinical signs of immunodeficiency within about five years; and (ii) no detectable HIV mRNA correlates with a low likelihood of the development of clinical signs of immunodeficiency for at least two years.

25. The method according to claim 24, wherein the therapeutic treatment comprises administration of an effective amount of an antiviral agent to the individual.

26. The method according to claim 25, wherein the antiviral agent is 3'-azido-3'-deoxythymidine.

27. The method according to claim 24, wherein the HIV is HIV-1.

28. The method according to claim 24, wherein the HIV mRNA is selected from the group consisting of multiply spliced (MS), unspliced (US), or single-spliced (SS) HIV mRNA.

29. The method according to claim 28, wherein the level of expression of HIV mRNA is determined by quantitating the amount of HIV mRNA by polymerase chain reaction.

30. The method according to claim 29, further comprising comparing the amount of HIV mRNA determined by polymerase chain reaction with an amount of a control RNA in parallel.

31. A method for monitoring a therapeutic treatment for AIDS comprising determining a level of expression of HIV messenger RNA (mRNA) in peripheral blood cells of an individual undergoing a therapeutic treatment for AIDS, comprising:

(a) determining a level of expression of HIV messenger RNA in peripheral blood cells obtained from the individual; and (b) correlating the level of expression of HIV messenger RNA with a prognosis for the time of onset of death; wherein no detectable HIV mRNA correlates with a low likelihood of the onset of death for at least two years.

32. The method according to claim 31, wherein the therapeutic treatment comprises administration of an effective amount of an antiviral agent to the individual.

33. The method according to claim 32, wherein the antiviral agent is 3'-azido-3'-deoxythymidine.

34. The method according to claim 31, wherein the HIV is HIV-1.

35. The method according to claim 31, wherein the HIV mRNA is selected from the group consisting of multiply spliced (MS), unspliced (US), or single-spliced (SS) HIV mRNA.

36. The method according to claim 35, wherein the level of expression of HIV mRNA is determined by quantitating the amount of HIV mRNA by polymerase chain reaction.

37. The method according to claim 36, further comprising comparing the amount of HIV mRNA determined by polymerase chain reaction with an amount of a control RNA in parallel.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: NO ( x i ) SEQUENCE DESCRIPTION: SEQ ID NO:1:

TCTCTAGCAG TGGCGCCCGA ACA    23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: YES ( x i ) SEQUENCE DESCRIPTION: SEQ ID NO:2:

TCTCCTTCTA GCCTCCGCTA GTC    23

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: NO ( x i ) SEQUENCE DESCRIPTION: SEQ ID NO:3:

CTTAGGCATC TCCTATGGCA GGAA     24

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: YES ( x i ) SEQUENCE DESCRIPTION: SEQ ID NO:4:

TTCCTTCGGG CCTGTCGGGT CCC     23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: NO ( x i ) SEQUENCE DESCRIPTION: SEQ ID NO:5:

CGAGCACAGA GCCTCGCCTT TGC     23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: YES ( i v ) ANTI-SENSE: YES ( x i ) SEQUENCE DESCRIPTION: SEQ ID NO:6:

CATAGGAATC CTTCTGACCC ATG     23